(12) United States Patent
Hackathorn, II

(10) Patent No.: US 10,478,233 B2
(45) Date of Patent: Nov. 19, 2019

(54) ADJUSTABLE HOOK

(71) Applicant: Alphatec Spine, Inc., Carlsbad, CA (US)

(72) Inventor: Thomas Hackathorn, II, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 15/813,790

(22) Filed: Nov. 15, 2017

(65) Prior Publication Data

US 2018/0132909 A1 May 17, 2018

Related U.S. Application Data

(60) Provisional application No. 62/422,618, filed on Nov. 16, 2016.

(51) Int. Cl.
*A61B 17/70* (2006.01)
*A61B 17/00* (2006.01)

(52) U.S. Cl.
CPC ...... *A61B 17/7065* (2013.01); *A61B 17/7032* (2013.01); *A61B 17/7056* (2013.01); *A61B 17/707* (2013.01); *A61B 17/7071* (2013.01); *A61B 2017/00407* (2013.01); *A61B 2017/00685* (2013.01)

(58) Field of Classification Search
CPC ............ A61B 17/7032; A61B 17/7034; A61B 17/7035; A61B 17/7037; A61B 17/7038; A61B 17/704; A61B 17/7043; A61B 17/7044; A61B 17/7046
USPC .......................... 606/246, 264–278, 300–321
See application file for complete search history.

(56) References Cited

U.S. PATENT DOCUMENTS

2016/0030086 A1* 2/2016 Mishra ............... A61B 17/7037
606/276

* cited by examiner

*Primary Examiner* — Julianna N Harvey
*Assistant Examiner* — Christina Negrellirodriguez
(74) *Attorney, Agent, or Firm* — Robert Winn

(57) ABSTRACT

A bone hook having a displaceable jaw is provided. The hook includes a rod receiving portion and main body with a jaw defining a slot for receiving a bone, and an actuator configured to vary the dimension of the slot. The actuator is configured to translate a rotation into an adjustment of a height of the slot thereby gripping or clamping a pedicle, lamina, or transverse process bone between the jaw and main body.

17 Claims, 10 Drawing Sheets

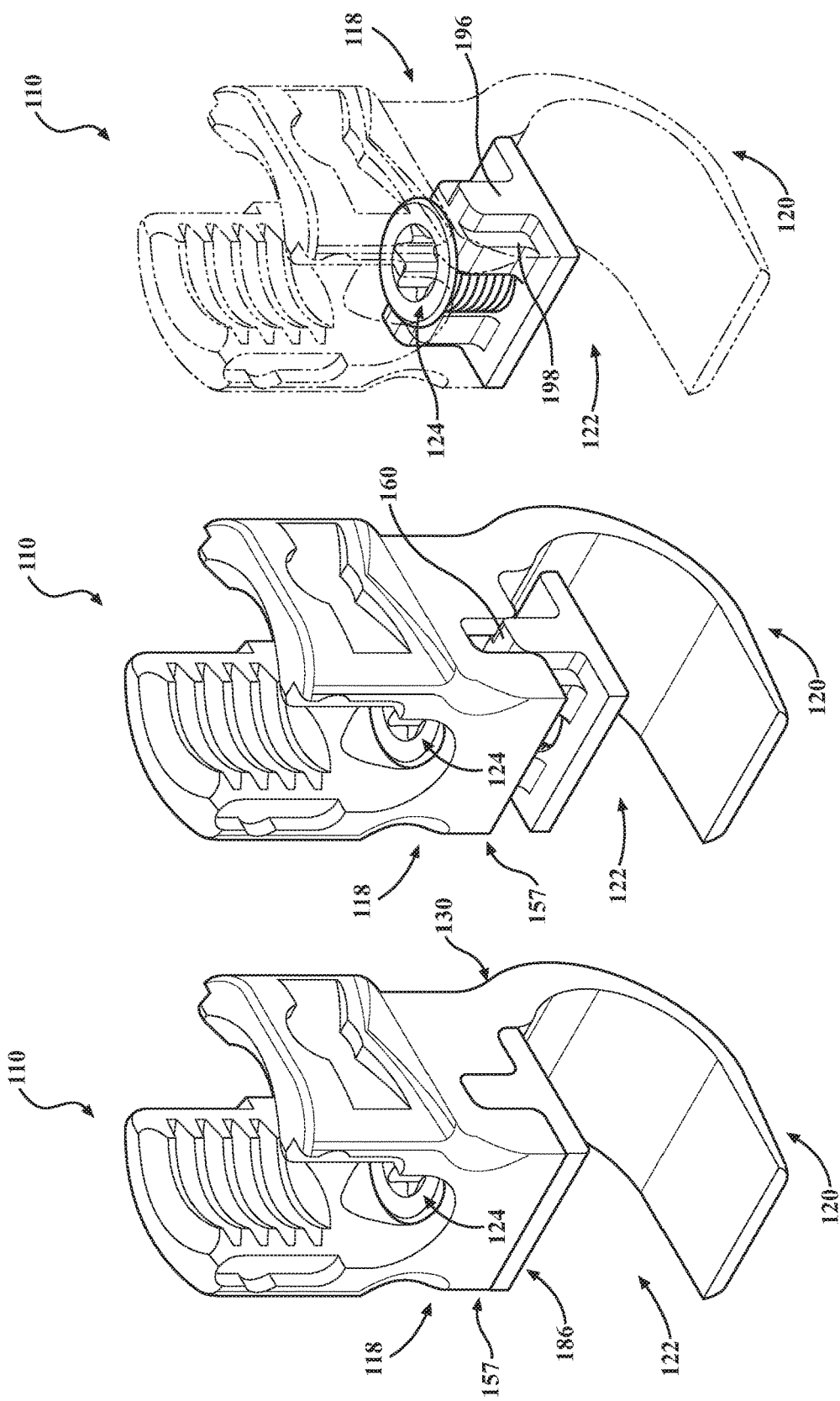

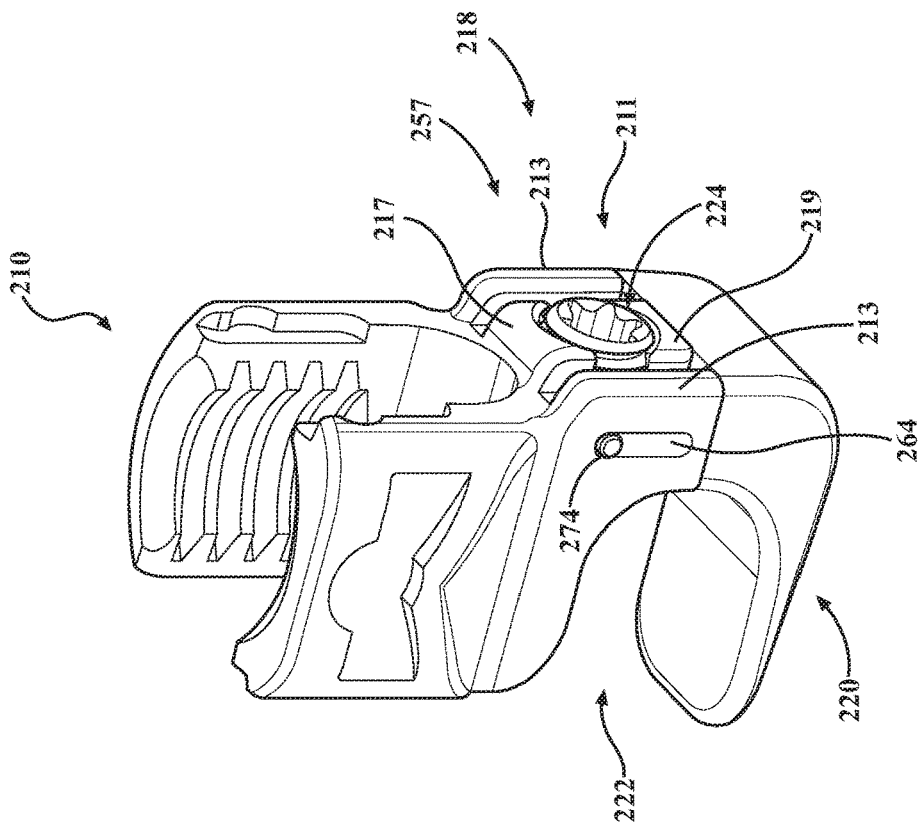
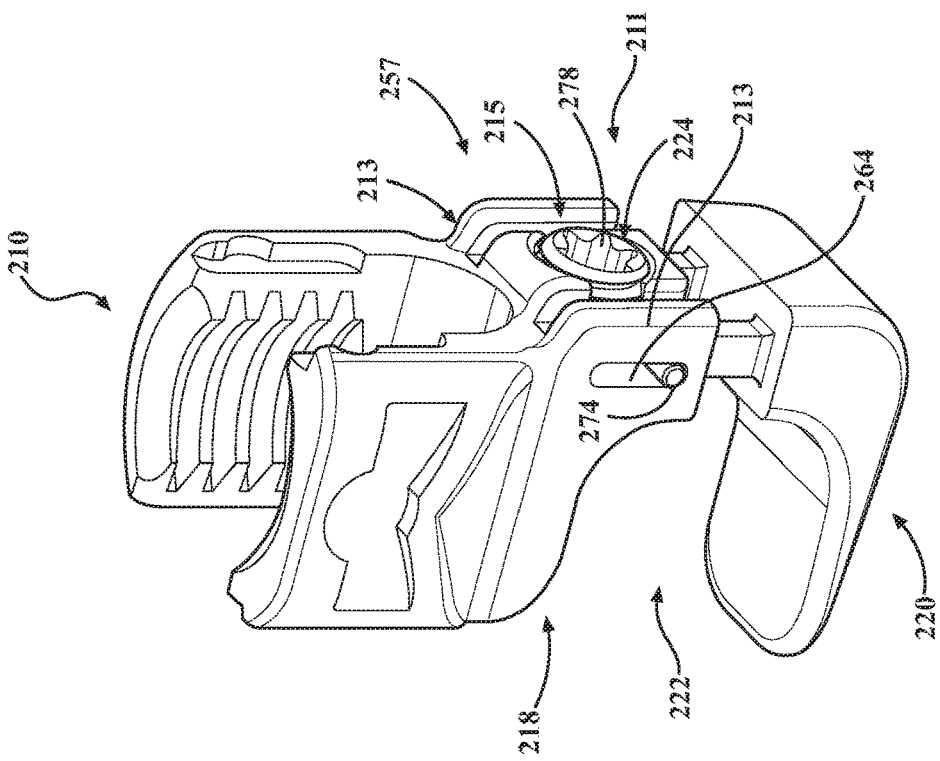
FIG. 3A
FIG. 3B

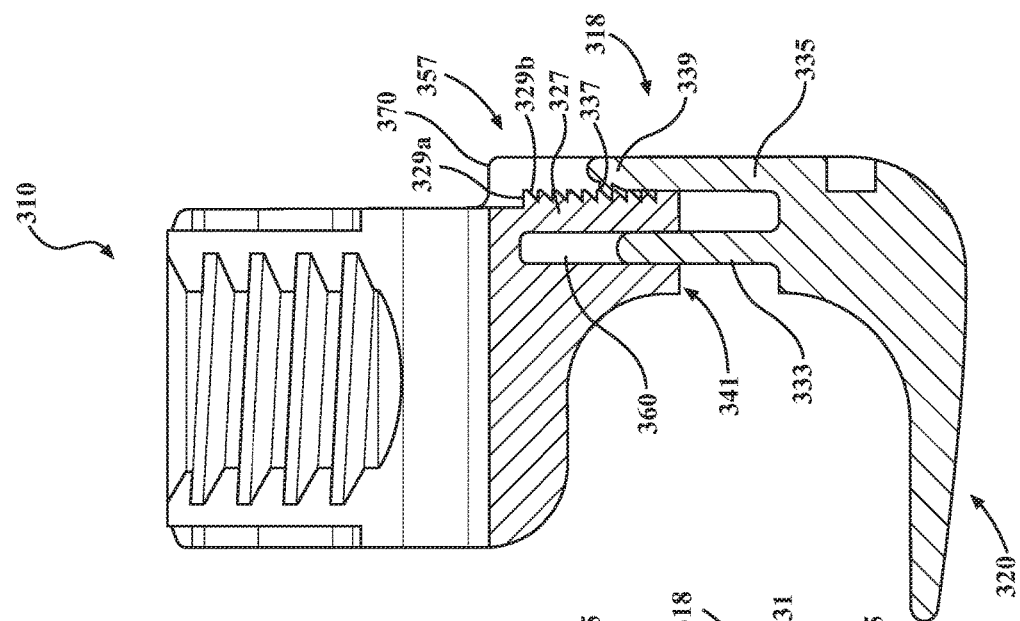
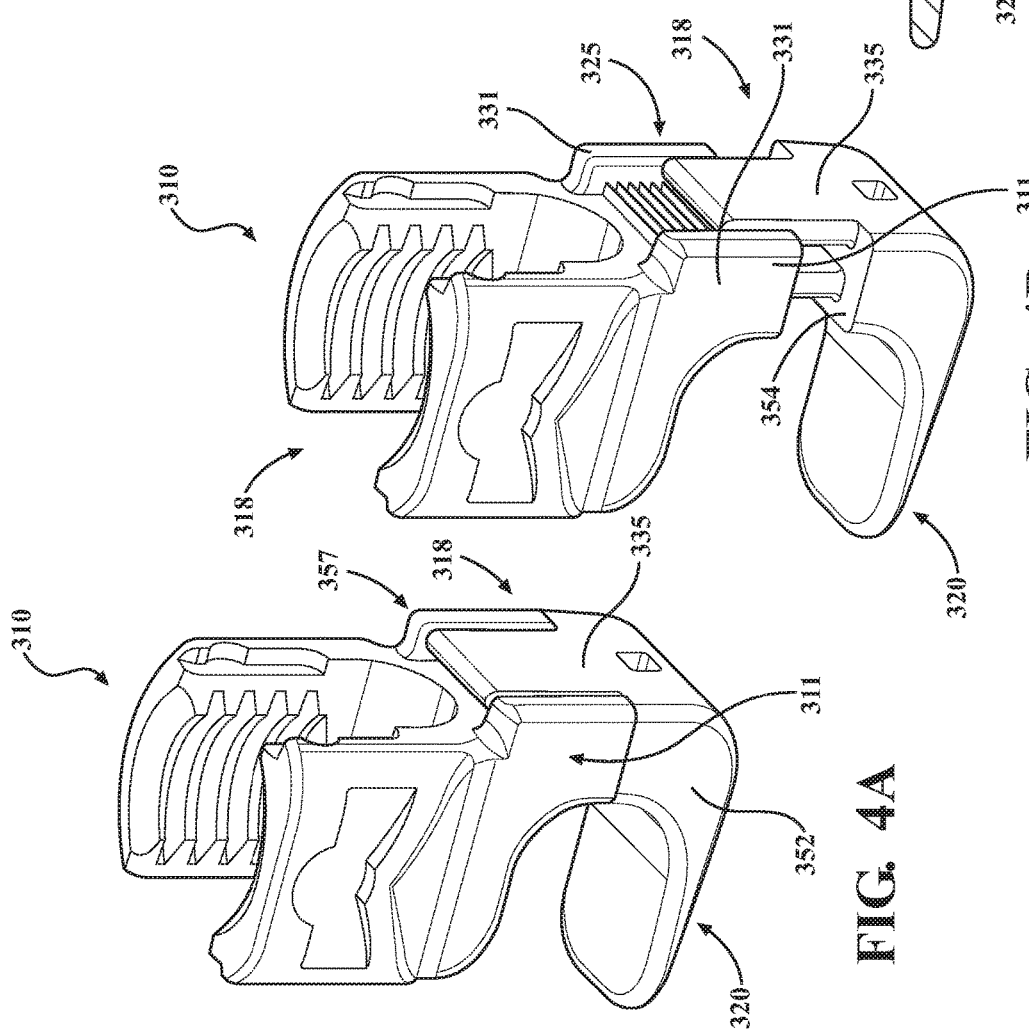

ADJUSTABLE HOOK

CROSS-REFERENCE TO RELATED APPLICATIONS

This application claims priority of U.S. Provisional Patent Application No. 62/422,618 filed Nov. 16, 2016, the contents of which are incorporated herein by reference.

FIELD OF THE INVENTION

The present invention relates to an adjustable hook for holding onto bone structure.

BACKGROUND OF THE INVENTION

Surgical bone hooks are commonly used in the treatment of a variety of spine related conditions and surgeries such as spinal deformity, scoliosis, and posterior approach surgeries. When a patient has a spinal fracture or structure deficiencies and abnormalities, the spinal vertebrae are typically too close together or spaced too far apart. The treatment of such a condition includes stabilizing the vertebrae in a correct position relative to one another. To accomplish this, the vertebrae must either be pushed towards each other or distracted from one another.

Surgeons use surgical bone hooks to hook and hold the pedicle, lamina, or transverse process bone of one vertebra into a desired location relative to an adjacent vertebrae. In particular, the hooks are hooked into the pedicle, lamina, or transverse process bones of adjacent vertebrae and each hook is fastened to a rod.

Spines vary in anatomical size and shape, and surgical bone hooks are currently manufactured in a variety of fixed sizes and shapes in an attempt to accommodate the anatomy of different patients from the lumbar to the thoracic spine. Nevertheless, current hooks are fixed and may not fit a patient correctly. Accordingly, it remains desirable to have a bone hook which is adaptable in its engagement feature so as to accommodate multiple pedicle bone dimensions.

SUMMARY OF THE INVENTION

The bone hook assembly includes a main body having a rod receiving portion, a jaw, and a slot defined between the main body and jaw. The slot is configured to receive a bone. The bone hook assembly further includes an actuator. The actuator is configured to vary dimensions of the slot so as to accommodate pedicle, lamina, or transverse process bones of varying sizes between the main body and jaw.

The rod receiving portion includes a pair of side walls defining a channel to receive a surgical rod. The side walls are threaded and configured to threadingly receive an externally threaded fastener, such as a set screw. The set screw threadingly engages the side walls to tighten down onto the rod; thus, positioning the rod firmly within the channel of the rod receiving portion.

In one embodiment, the actuator includes a fastener with external threads, and a threaded bore disposed on either the main body or the jaw. The actuator is configured to translate a rotational movement of the fastener to an axial variation of the slot. The axial variation of the slot may be achieved by bringing the jaw closer to the main body, or a plate closer to the jaw.

In one embodiment, the jaw is slidably disposed with respect to the main body, and the actuator is configured to fix the jaw so as to provide a desired dimension of the slot. The fixation of the jaw may be achieved by a clamping force applied to the jaw or a ratchet mechanism fixing the jaw in a desired position.

Accordingly, the bone hook assembly is configured to vary dimensions of the slot to accommodate multiple pedicle, lamina, or transverse process bone dimensions. Further, adjusting the dimension of the slot may be done easily as the actuator is accessible.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings where like structure is indicated with like reference numerals and in which:

FIG. 2A illustrates a front view of a hook according to one or more embodiments disclosed and described herein in a closed position;

FIG. 2B illustrates a front view of the hook in FIG. 2A in the expanded position;

FIG. 2C illustrates a sectional view of the hook in FIG. 2A;

FIG. 3A illustrates a side view of a hook according to one or more embodiments disclosed and described herein in an expanded position;

FIG. 3B illustrates a side view of the hook in FIG. 3A in the closed position;

FIG. 4A illustrates a side view of a hook according to one or more embodiments disclosed and described herein in a closed position;

FIG. 4B illustrates a side view of the hook in FIG. 4A in the expanded position;

FIG. 4C illustrates a sectional view of the hook in FIG. 4A; and

DETAILED DESCRIPTION OF THE PREFERRED EMBODIMENTS

Figures 1A, 1B:
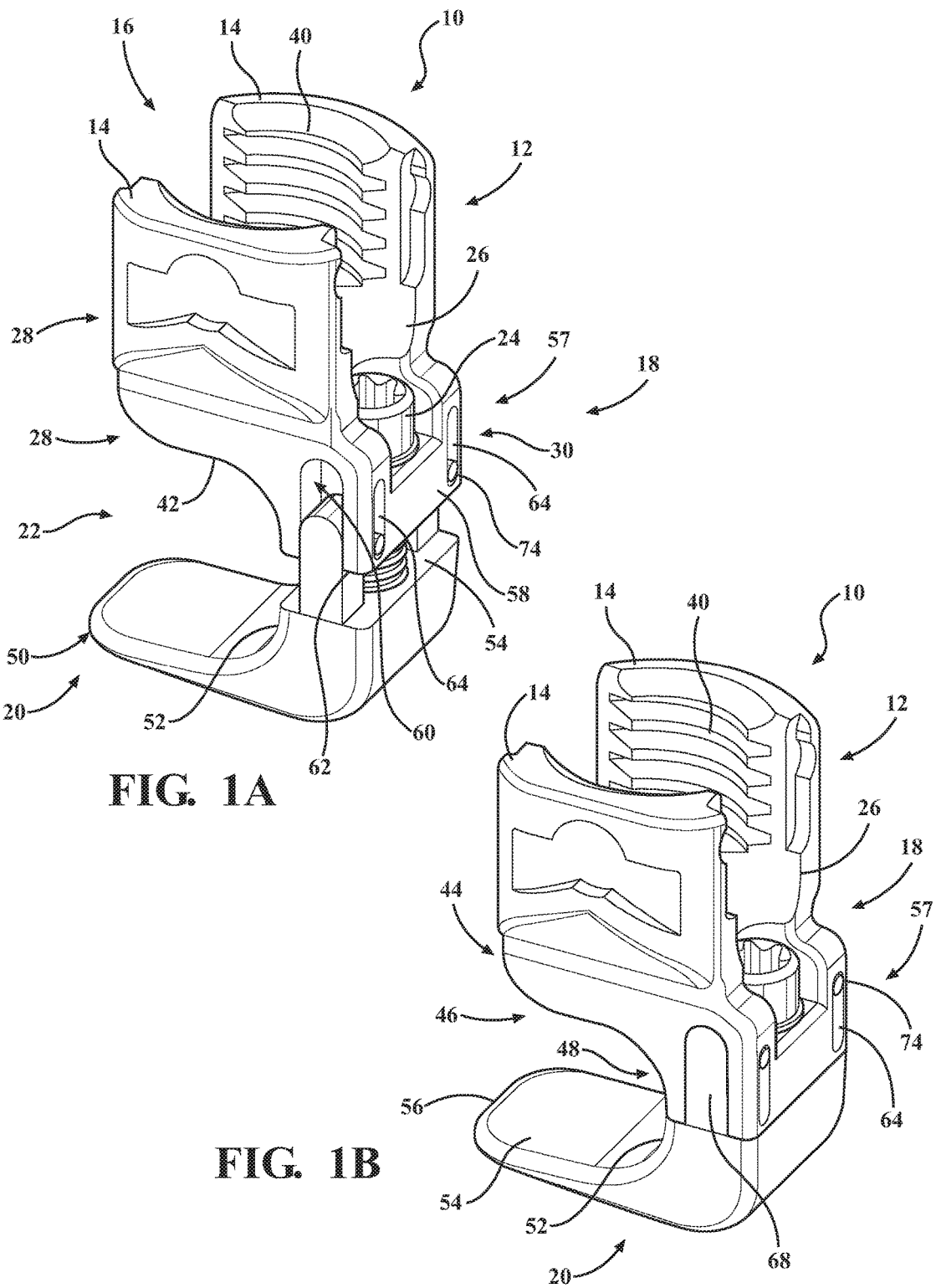
FIG. 1A illustrates a side view of a hook according to one or more embodiments disclosed and described herein in a closed position.
FIG. 1B illustrates a side view of the hook in FIG. 1A in the expanded position.
Figure 1C:
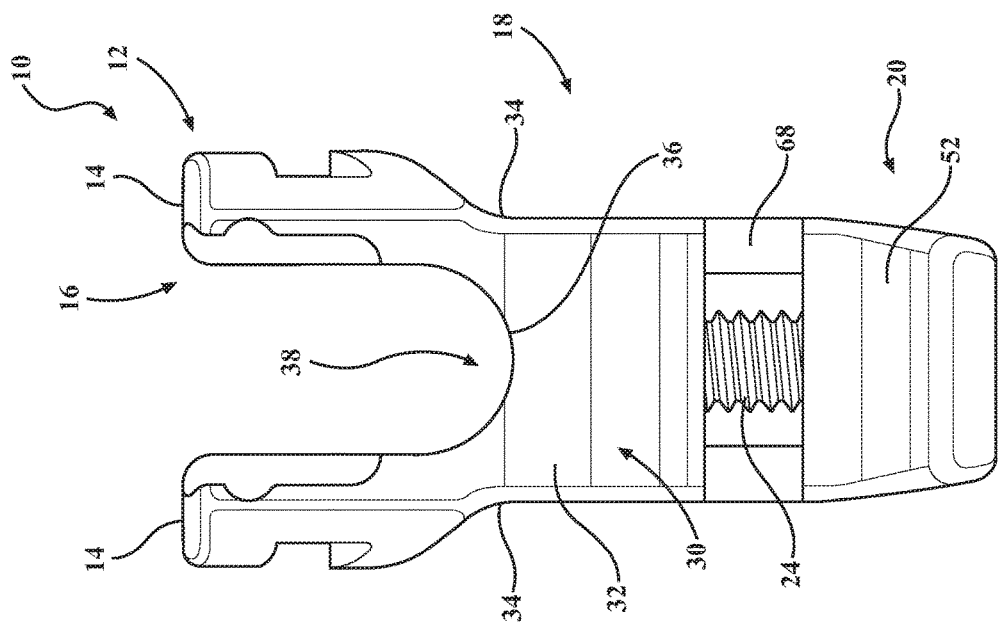
FIG. 1C illustrates a front view of the hook in FIG. 1A in the closed position.
Figure 1D:
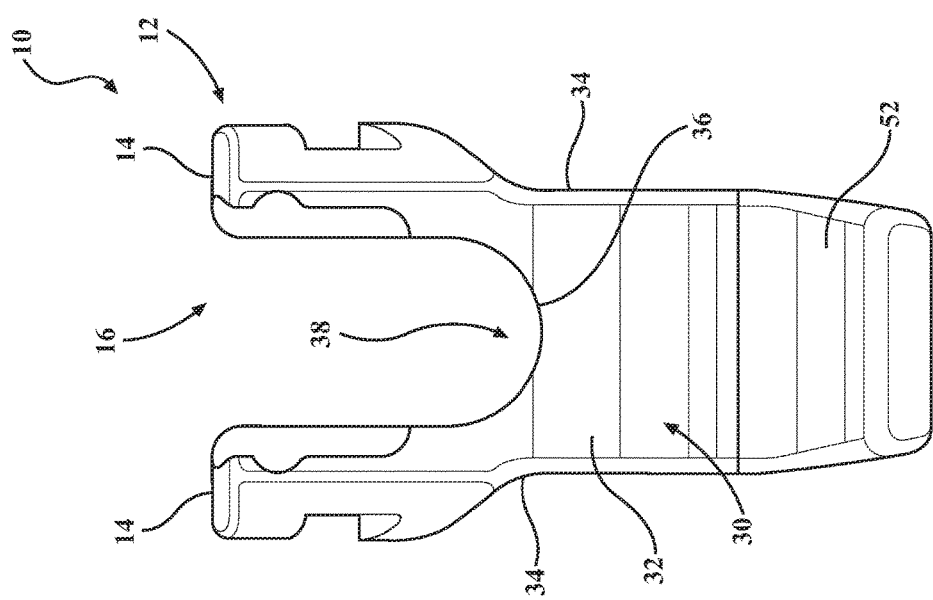
FIG. 1D illustrates a front view of the hook in FIG. 1A in the expanded position.
Figure 1E:
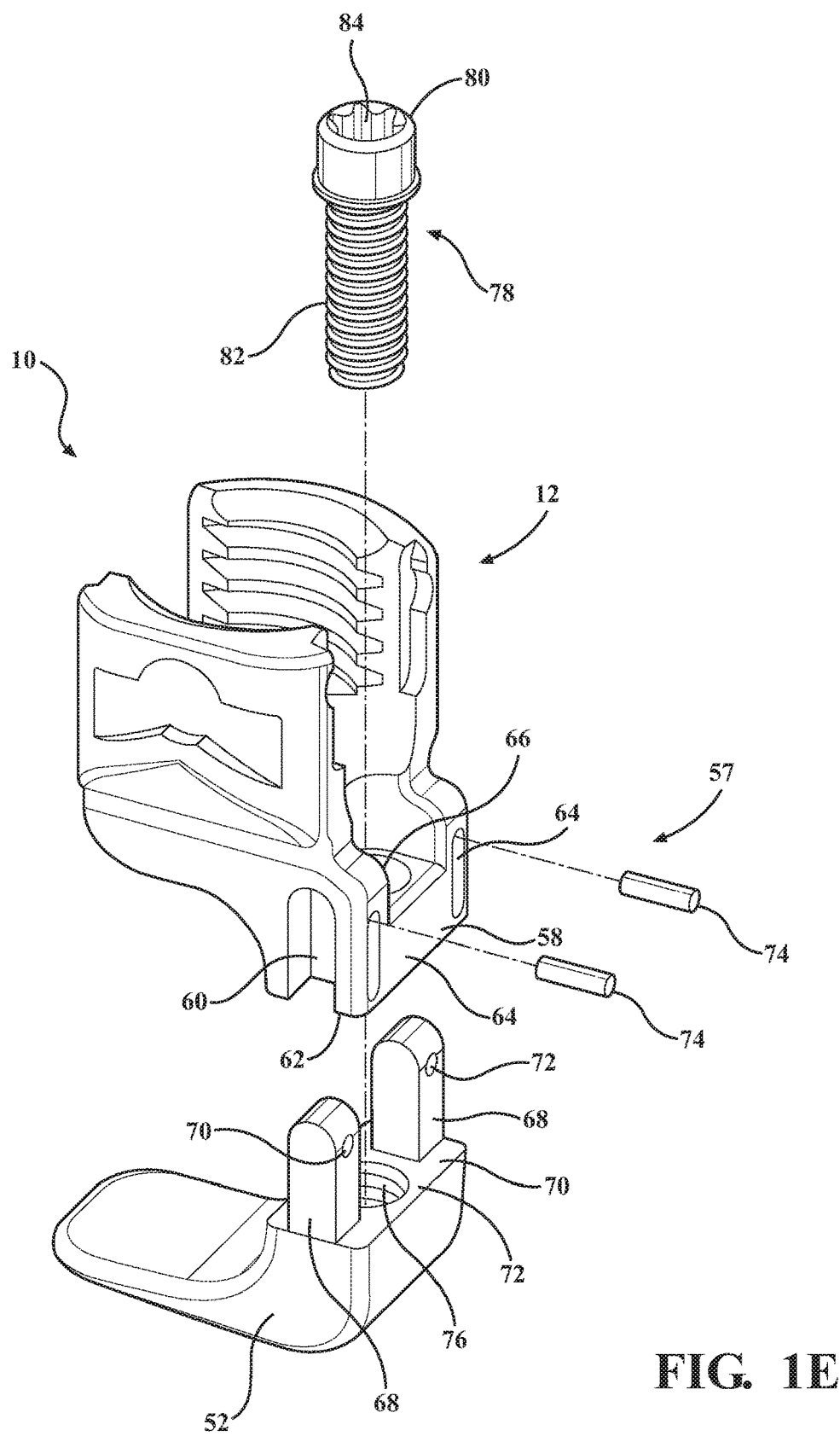
FIG. 1E illustrates an exploded view of the hook in FIG. 1A.
Figure 2D:
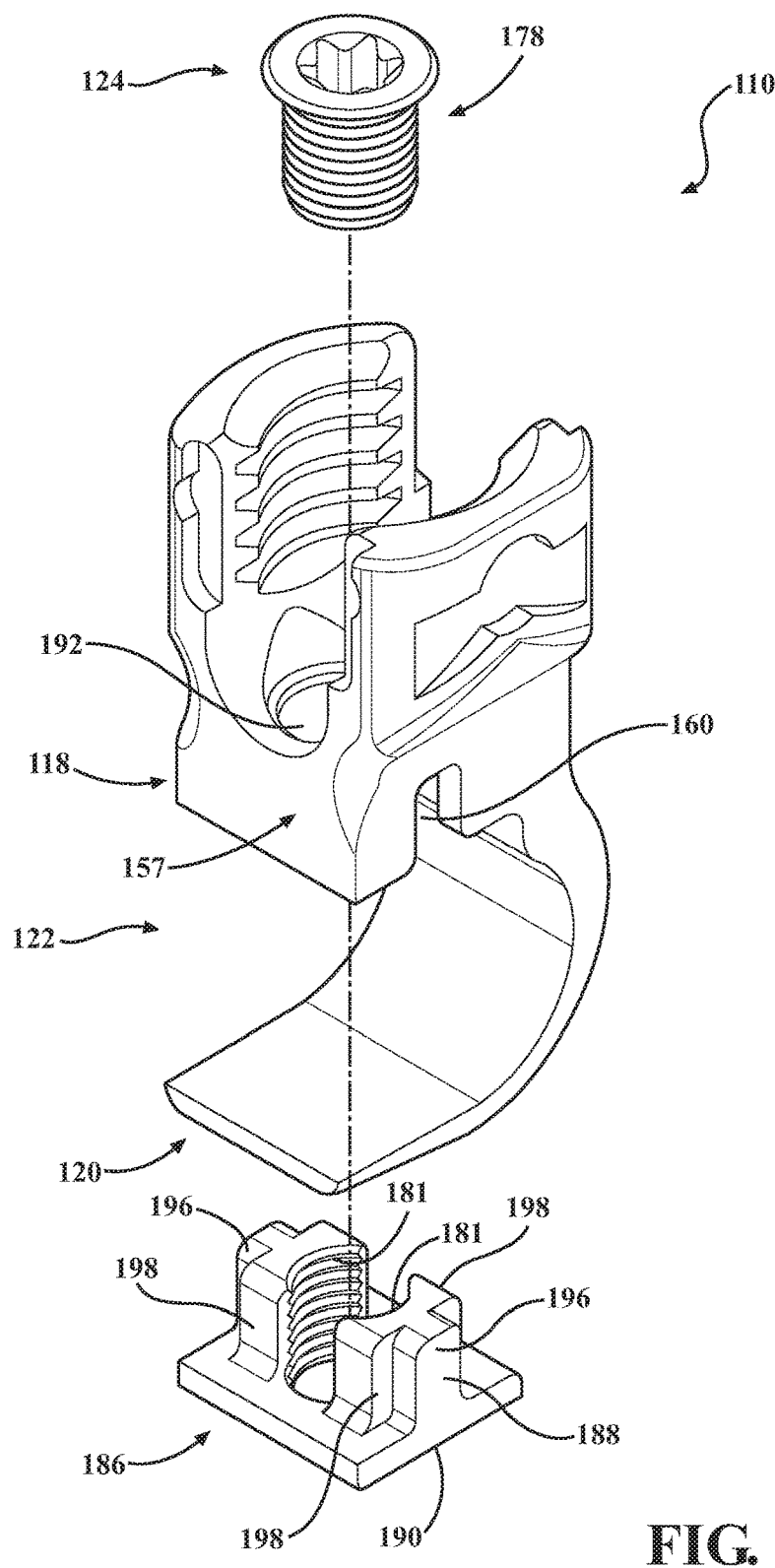
FIG. 2D illustrates an exploded view of the hook in FIG. 2A.

An adjustable bone hook assembly is provided. The bone hook assembly includes a main body having a rod receiving portion and a jaw defining a slot therebetween for receiving a pedicle, lamina, or transverse process bone. The dimension of the slot may be varied so as to accommodate pedicle, lamina, or transverse process bones of different dimensions. In particular, the height of the slot may be varied so as to accommodate pedicle, lamina, or transverse process bones of different sizes. In one embodiment, rotation of an actuator is translated into a variation of the height of the slot. In another embodiment, the jaw is slidably attached the main body, and the actuator fixes the jaw in a desired position relative to the main body.

As used herein, the term "height" refers to the axial length of the slot as measured by the distance between a bottom surface of the main body and a top surface of the jaw. The terms "bottom" and "top" are made in reference to the orientation of the part as depicted in the accompanying figures. The terms "back" and "front" are made in reference to the function of the bone hook assembly, wherein "front" refers to the surface of the bone hook assembly open to the slot and "back" refers to the surface of the bone hook assembly opposite the "front".

With reference now to FIGS. 1A-1E, a first embodiment of a bone hook assembly 10 is provided. The bone hook assembly 10 includes a rod receiving portion 12. The rod receiving portion 12 includes a pair of receiving walls 14 defining a channel 16 to receive a rod (not shown). The receiving walls 14 are threaded for receiving an externally threaded fastener, such as a set screw (not shown). The set screw threadingly engages the receiving walls 14 so as to clamp onto the rod; thus, positioning the rod firmly within the channel 16. The bone hook assembly 10 may be formed of a durable material approved for use in surgical procedures, illustratively including titanium.

The bone hook assembly 10 further includes a main body 18 and a jaw 20. The main body 18 is disposed beneath the rod receiving portion 12. The jaw 20 is spaced apart from the main body 18 so as to define a slot 22 and an actuator 24 is configured to translate a rotational movement to adjust the height of the slot 22 so as to clamp onto pedicle bones of different dimensions.

A bottom surface 42 of the main body 18 is adapted to provide a clamping force onto the pedicle, lamina, or transverse process bone. The bottom surface 42 of the main body 18 includes a front end 44, a mid-portion 46 and a back end 48. The front 44 end may be convex so as to facilitate the entry of the pedicle bone within the slot 22. The mid-portion 46 is disposed between the front end 44 and the back end 48 and is shown as being generally planar. However, it should be appreciated that the mid-portion 46 may be configured with teeth to help retain the pedicle bone within the slot 22.

The jaw 20 includes a clamping member 50 which is orthogonal to a back wall 52. In embodiments, the clamping member 50 is a generally planar member that is orthogonal to the back wall 52. The clamping member 50 includes a top surface 54 adapted to engage the pedicle bone. The top surface 54 is shown as having a front 56.

Still referring to FIGS. 1A-1E, and stated above, the bone hook assembly 10 is configured to translate rotational movement of the actuator 24 to adjust the height of the slot 22 so as to allow the bone hook assembly 10 to accommodate pedicle, lamina, or transverse process bones of different dimensions. Particularly, the main body 18 includes a receiving portion configured to slidingly receive the jaw 20 such that the jaw 20 slides up and down.

The receiving portion 57 is disposed on a back wall 30 of the main body 18. The receiving portion 57 includes a receiving body 58 generally centered within the receiving portion 57. The receiving portion 57 includes an elongated slot 60 disposed on opposite sides of the receiving portion 57. Each of the elongated slots 60 is open to a bottom end 62 of the receiving portion 57. The interior of the elongated slots 60 are closed by the receiving body 58 and also open to the outer surface of the receiving portion. The receiving portion 57 further includes a pair of pin slots 64. The pin slots 64 extend along the axial length of a respective elongated slot 60 so as to be open to a corresponding elongated slot 60. The pin slots 64 are closed at each end. The receiving body 58 includes a first bore 66 extending parallel to the elongated slots 60.

The jaw 20 includes a pair of tabs 68. The tabs 68 are disposed on opposite sides of a top surface 70 of the back wall 52 of the jaw 20 and may be integrally formed with the jaw 20. The tabs 68 are configured to slide within a respective elongated slot 60. The tabs 68 include a pin hole 72. A pin 74 is configured to engage the pin hole 72. The back wall 52 of the jaw 20 includes a threaded bore 76. The threaded bore 76 is configured to register with the first bore 66 when and the pair of tabs 68 are positioned within the elongated slots 60 and the jaw 20 is coupled to the receiving portion 57. A pair of pins 74 are disposed in respective pin holes 72. The pins 74 have an axial length longer that the thickness of the tabs 68 so as to extend and ride within the corresponding pin slot 64. As the pin slots 64 are closed at each end, the jaw 20 has a height displacement equal to the length of the pin slot 64.

The actuator 24 is configured to translate a rotational movement into an axial displacement of the jaw 20 with respect to the main body 18. In particular, the actuator 24 is a screw 78 having a head 80 and a shaft 82. The shaft 82 is threaded. The head 80 includes an engagement member 84 configured to engage a tool such as, but not limited to, a hex key wrench, a screw driver, and the like. The shaft 82 is configured to threadingly engage the threaded bore 76 of the jaw 20.

In operation, the jaw 20 is slidably coupled to the main body 18 by inserting the tabs 68 into the respective elongated slots 60 of the receiving portion 57. The pins 74 are coupled to the pin holes 72 of the tabs so as to slidably retain the jaw 20 to the main body 18. The screw 78 is disposed in the first bore 66 of the receiving body 58 and threaded into the threaded bore 76 of the jaw 20. A tool, e.g., a hex key wrench (not shown) is used to engage the engagement member 84 of the head 80 of the screw 78, wherein rotation of the screw 78 adjusts the height of the slot 22.

FIG. 1A shows the bone hook assembly 10 in a fully open position and FIG. 1B shows the bone hook assembly 10 in a closed position. It should be appreciated that the height of the slot 22 may be adjusted between the fully open position and the closed position by rotation of the screw 78 in a clockwise or counterclockwise direction, wherein the jaw 20 is prevented from rotation by the engagement of the tabs 68 within the respective elongated slot 60. Accordingly, the shaft 82 of the screw is able to engage the threaded bore 76 of the jaw 20, moving the jaw 20 up and down the pin slots 64 and the respective tabs 68 of the receiving portion 57.

With reference now to FIGS. 2A-2D a second embodiment of a bone hook assembly 110 is illustratively depicted, wherein like elements from FIGS. 1A-1E are referenced by like numbers increased by 100. As stated above, in the first embodiment, the bone hook assembly 110 is configured translate a rotational movement to adjust the height of the slot 122 so as to allow the bone hook assembly 110 to accommodate pedicle, lamina, or transverse process bones of different dimensions. As with the first aspect, an actuator 124 is used to translate a rotational movement into a height adjustment of the slot 122.

The jaw 120 is fixed to the back wall 130 of the main body 118. The receiving portion 157 is integrated into the main body 118. The receiving portion 157 is configured to receive a clamping plate 186. The receiving portion 157 includes a pair of elongated slots 160 disposed on opposing side walls.

A clamping plate 186 is slidably coupled to the receiving portion 157 and is configured to cooperate with the jaw 120 so as to clamp onto a pedicle, lamina, or transverse process bone. The distance between the clamping plate 186 and the jaw 120 defines the height of the slot 122. The clamping plate 186 includes a pair of tabs 188 and a plate 190 generally orthogonal to the pair of tabs 188. The plate 190 is configured to apply a clamping force onto the pedicle, lamina, or transverse process bone. The plate 190 is illustratively shown as having a uniform and planar surface. However, it should be appreciated that plate 190 may be configured with teeth to help retain the pedicle bone within the slot 122.

The tabs 188 are configured to slide within the respective elongated slots 160 of the receiving portion 157. The tabs 188 are disposed on opposite sides of the clamping plate 186. The receiving portion 157 includes a through-bore 192 configured to accommodate a screw 178 and the tabs 188. The clamping plate 186 is further configured to threadingly engage the screw 178.

In one embodiment, an inner surface 181 of each of the tabs 180 are threaded. FIGS. 2A-2E depict an embodiment, wherein each tab 180 includes an outer rib 196 and a shoulder 198. The outer rib 196 is dimensioned to slide within the elongated slots 160 of the receiving portion 157. The shoulder 198 is configured to slide within the through-bore 192 of the receiving portion 157. The inner surface of the shoulders 198 is arcuate and threaded. It should be appreciated that the clamping plate 186 is depicted for illustrative purposes and may be modified without deviating from the scope of the appended claims. For instance, the shoulders 198 may be joined together to form a cylindrical body with an open top, wherein the inner wall of the cylindrical body is threaded.

The actuator 124 is a screw 178. The screw 178 is disposed within the through-bore 192 of the receiving portion 157. The screw 178 is also threadingly engaged with the threaded inner surface of the shoulders 198. Rotation of the screw 178 axially displaces the clamping plate 186 with respect to a shaft of the screw 178.

In operation, the bone hook assembly 110 is positioned onto a pedicle, lamina, or transverse process bone by insertion of the pedicle, lamina, or transverse process bone into the slot 122. The height of the slot 122 may be adjusted by rotation of the screw 178 wherein the clamping plate 186 is advanced towards the pedicle, lamina, or transverse process bone, clamping the pedicle, lamina, or transverse process bone between the clamping plate 186 and the fixed jaw 120. FIG. 2A shows the bone hook assembly 110 in a fully open position, wherein the height of the slot 122 is at its maximum. In the open position, the clamping plate 186 is nested against the receiving portion 157. FIG. 2B shows the clamping plate 186 in a closed position, wherein the height of the slot 122 is at its minimum. Accordingly, the bone hook assembly 110 is configured to clamp onto a pedicle, lamina, or transverse process bone configured to fit within the adjustable height of the slot 122.

With reference now to FIGS. 3A-3E an illustrative depiction of a third embodiment of the bone hook assembly 210 is provided wherein like elements from FIGS. 1A-1E are referenced by like numbers increased by 200. In the third embodiment, the jaw 220 is slidably disposed with respect to the main body 218, and the actuator 224 is configured to fix the jaw 220 so as to provide a desired dimension of the slot 222. Particularly, fixation of the jaw 220 may be achieved by a clamping force applied to the jaw 220.

The receiving portion 257 is disposed on a back end 211 of the main body 218. The receiving portion 257 is configured to slidingly receive the jaw 220. The receiving portion 257 includes a pair of fins 213 and a receiving body 215. The pair of fins 213 are disposed on opposite sides of the receiving portion 257. The receiving body 215 is disposed between and spaced apart from the pair of fins 213 so as to define an elongated slot 260. The elongated slots 260 are open on a bottom and a top end. Each of the pair of fins 213 includes a pin slot 264. The pin slots 264 are closed at each end and open to a corresponding elongated slot 260.

The receiving body 215 includes an upper body member 217 and a lower body member 219. The upper body member 217 is spaced apart from the lower body member 219. The upper body member 217 and the lower body member 219 include an inner wall 221 which are opposite of each other. The inner walls 221 are generally arcuate and threaded. The inner walls 221 are threaded so as to define a threaded bore 276. The threaded bore 276 extends along an axis generally orthogonal to the axial length of the pin slots 264.

The jaw 220 includes a pair of tabs 268. The tabs 268 are generally elongated members extending from a top surface 254 of the back wall 252 of the jaw 220. The tabs 268 include a pin hole 272. The pin holes 272 may extend through opposing sides of the respective tabs 268.

The bone hook assembly 210 further includes a pair of pins 274. The pins 274 are configured to fittingly engage a pin hole 272 of a respective tab 268. The pins 274 have a length longer than the width of the tabs 268 so as to extend past the tab 268 and slide within the bounds of the pin slots 264.

The bone hook assembly 210 further includes an actuator 224. The actuator 224 is configured to bias the tabs 268 against the receiving portion 257 so as to create a friction lock, locking the tabs 268 in a desired position with respect to the receiving portion 257. In one embodiment, the actuator 224 is a set screw 278. The set screw 278 has a diameter greater than the width of the upper and lower body members 217, 219 of the receiving body 215 so as to project radially with respect to an outer surface of the receiving body 215.

Figure 3D:
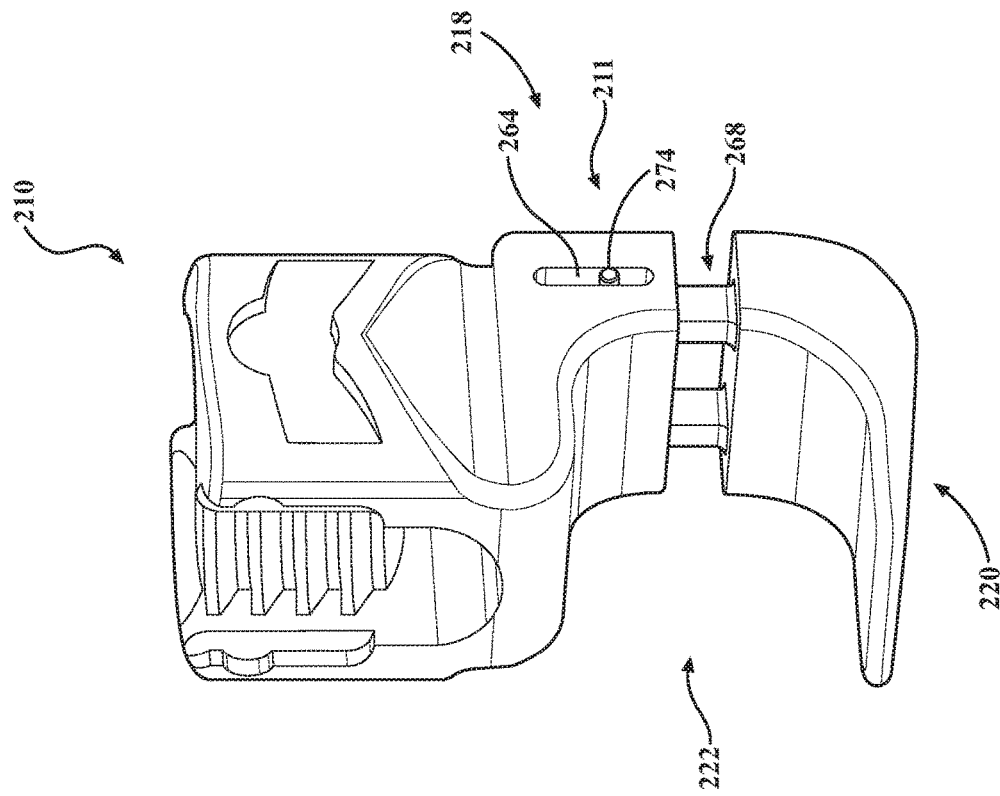
FIG. 3D illustrates a front view of the hook in FIG. 3A.
Figure 3C:
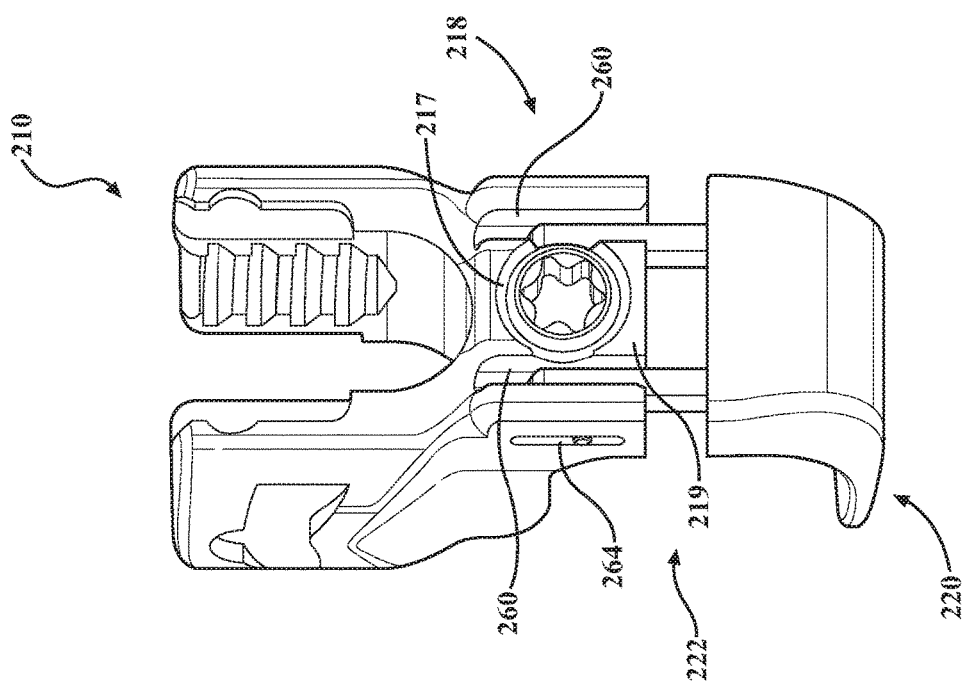
FIG. 3C illustrates a back view of the hook in FIG. 3A.
Figure 3E:
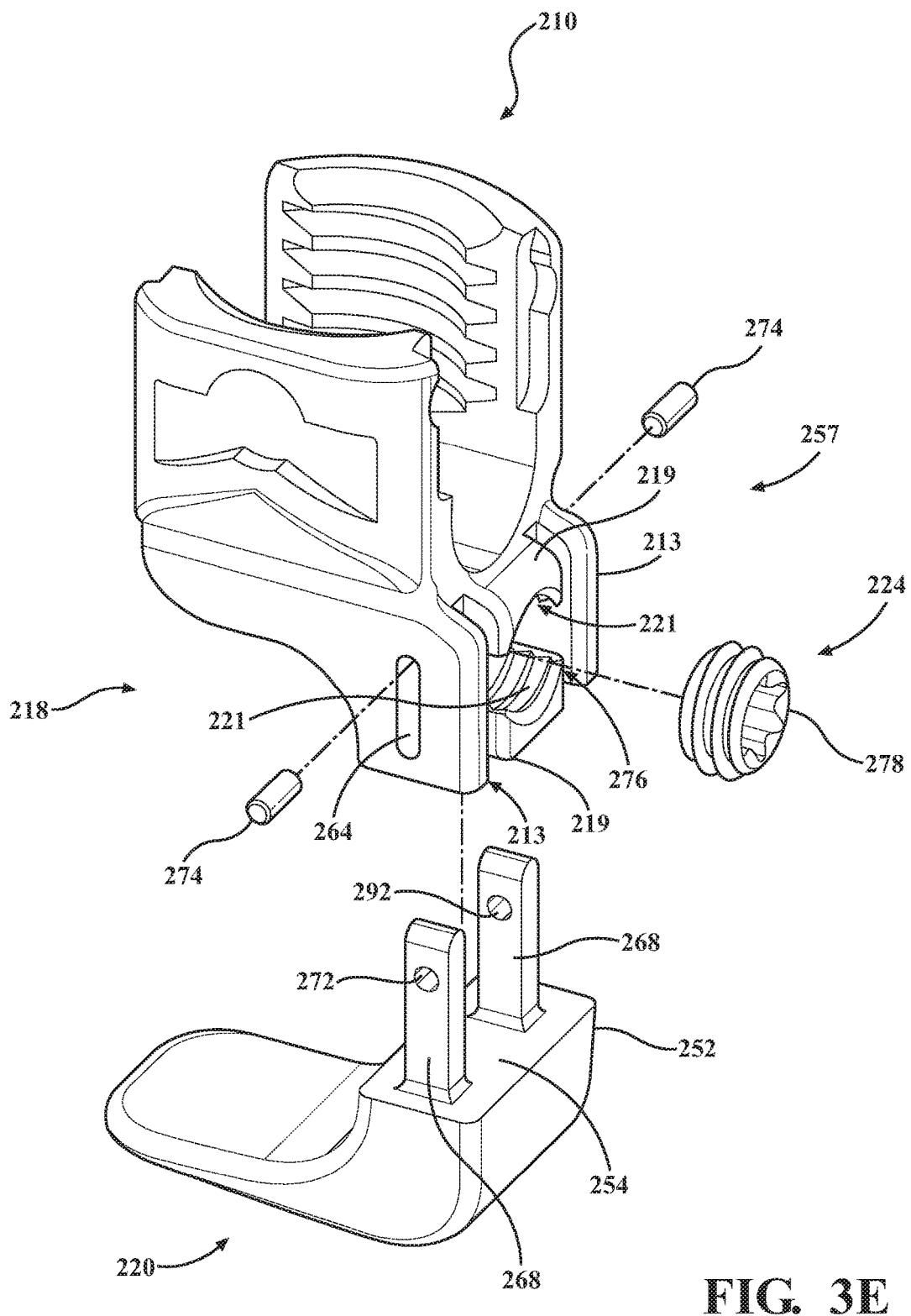
FIG. 3E illustrates an exploded view of the hook in FIG. 3A.
Figure 4D:
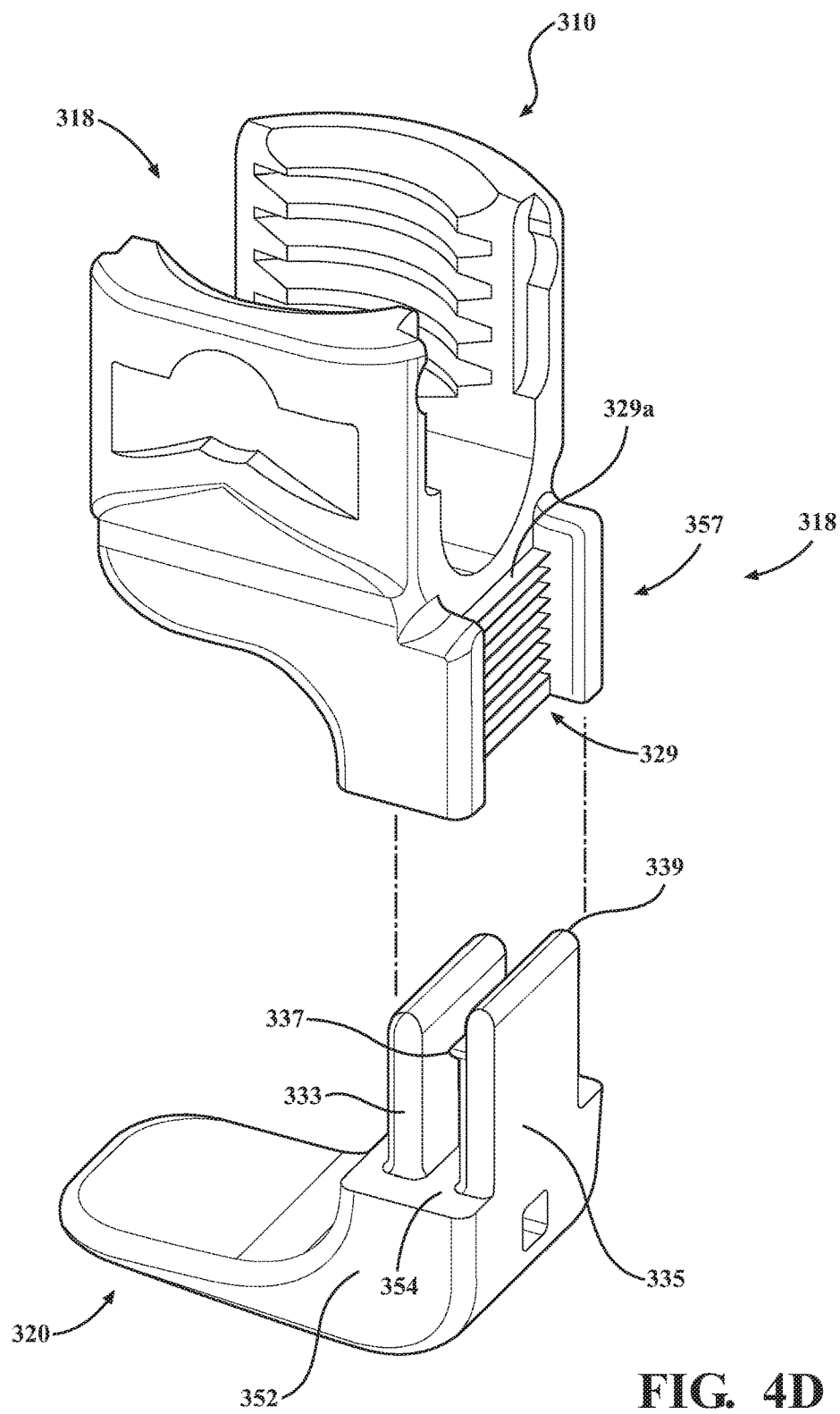
FIG. 4D illustrates an exploded view of the hook in FIG. 4A.

In operation, the jaw 220 is slid within the elongated slots 260 so as to generate a desired height. The set screw 278 may then be threaded into the threaded bore 276, wherein the edge of the set screw 278 extending beyond the outer surface of the receiving portion 257 engages a respective tab 268. As the set screw 278 is further threaded into the threaded bore 276, the biasing force of the set screw 278 on the tabs 268 increases until a friction locking condition is achieved, fixing the tabs 268 with respect to the receiving portion 257. FIGS. 3A, 3C and 3D show the bone hook assembly 210 in a fully open position, wherein the height of the slot 222 is at its maximum. FIG. 3B shows the bone hook assembly 210 in a closed position wherein the height of the slot 222 is at its minimum. Accordingly, the bone hook assembly 210 is configured to clamp onto a pedicle, lamina, or transverse process bone configured to fit within the adjustable height of the slot 222.

With reference now to FIGS. 4A-4D, a fourth embodiment of a bone hook assembly 310 is illustratively depicted, wherein like elements from FIGS. 1A-1E are referenced by like numbers increased by 300. In fourth embodiment, a ratchet mechanism 325 fixes the jaw 320 in a desired position.

The receiving portion 357 is disposed on a back end 311 of the main body 318. The receiving portion 357 includes an elongated slot 360. The elongated slot 360 extends along an axial length of the receiving portion 357 as measured between a top surface 370 of the receiving portion 357 and a bottom surface 341 of the receiving portion 357.

A back wall 327 of the receiving portion 357 includes a plurality of teeth 329. The teeth 329 include a top contact surface 329a with is generally orthogonal to the back wall 327, and an angled surface 329b extending from the top contact surface 329a to the back wall 327. The receiving portion 357 further includes a pair of receiving walls 331 spaced apart from each other. The receiving walls 331 extend from the back wall 327 of the receiving portion 357.

The jaw 320 is slidably coupled to the receiving portion 357. The jaw 320 includes a guide 333 and a catch 335. The guide 333 and the catch 335 project from a top surface 354 of the back wall 352 of the jaw 320. The guide 333 is a generally planar member and is configured to slidingly fit within the elongated slot 360 of the receiving portion 357.

The catch 335 is also an elongated member spaced apart from the guide 333. The catch 335 may be formed of a durable and resilient material. The catch 335 has a width configured to fit between the pair of receiving walls 331. The catch 335 includes a lip 337 disposed on a distal end 339 of the catch 335. The lip 337 is configured to engage the teeth 329 so as to fix the jaw 320 in a desired position with respect to the main body 318. In particular the lip 337 is configured to engage the top contact surface 329a of any one of the plurality of teeth 329 so as to retain the jaw 320 in the desired position.

In operation, the jaw 320 may be coupled to the main body 318 by engagement of the lip 337 of the catch 335 with any one of the plurality of teeth 329. FIG. 4A shows the bone hook assembly 310 in a closed position, wherein the height of the slot 322 is at its minimum. FIGS. 4B and 4C shows the bone hook assembly 310 in an open position wherein the height of the slot 322 is at its maximum. Accordingly, the bone hook assembly 310 is configured to clamp onto a pedicle, lamina, or transverse process bone positioned within the adjustable height of the slot 322.

The height of the slot 322 may be set by engagement of the lip 337 to any one of the top contact surfaces 329a of the teeth 329. To adjust the height of the slot 322, the catch 335 is pulled away from the teeth 329 and the jaw 320 may be slid to the desired position. Alternatively, the catch 335 may be positioned so as to engage the top contact surface 329a closest to the bottom surface 341 of the receiving portion 357, wherein the pedicle, lamina, or transverse process bone is inserted into the slot 322, and the jaw 320 is simply pressed upwardly until the pedicle, lamina, or transverse process bone is clamped between the jaw 320 and the main body 318. Once released, the height of the slot 322 is set by the engagement of the catch 335 with the teeth 329.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

I claim:

1. A bone hook assembly adaptable to engage any one of a plurality of pedicle, lamina, or transverse process bones, each of the plurality of pedicle, lamina, or transverse process bones being dimensioned different than the other, the bone hook assembly comprising:
    a main body having a rod receiving portion;
    a jaw spaced apart from the main body so as to define a slot for receiving one of the plurality of pedicle, lamina, or transverse process bones, wherein the slot has a height;
    an actuator configured to adjust the height of the slot;
    a pair of tabs on the jaw; and
    a receiving portion having elongated slots;
    wherein the actuator is configured to translate a rotation into an adjustment of the height of the slot; and
    wherein the receiving portion is configured to slidingly receive the jaw wherein the pair of tabs are configured to slide into a respective elongated slot.

2. The bone hook assembly as set forth in claim 1, further comprising a pair of pins, a pair of pin slots on the receiving portion, and a pair of pin holes in the pair of tabs, and wherein the pair of pins disposed in the pair of pin holes are configured to extend into a corresponding pin slot.

3. The bone hook assembly as set forth in claim 1, further comprising a bore located in the receiving portion and a threaded bore in the jaw, and wherein the bore is configured to register with the threaded bore when the jaw is coupled to the receiving portion.

4. The bone hook assembly as set forth in claim 3, wherein the actuator is a screw disposed in a first bore of the receiving portion and threaded into the threaded bore of the jaw.

5. The bone hook assembly as set forth in claim 1, further comprising a clamping plate, wherein the receiving portion is integrated into the main body and wherein the receiving portion is configured to slidingly receive the clamping plate.

6. The bone hook assembly as set forth in claim 5, wherein the receiving portion includes a through-bore.

7. The bone hook assembly as set forth m claim 6, wherein the clamping plate is configured to threadingly engage a screw.

8. The bone hook assembly as set forth in claim 7, wherein the actuator is the screw disposed in the through-bore and threadingly engaged with the clamping plate.

9. The bone hook assembly as set forth in claim 1, further comprising a pair of pins, a pair of pin slots on the receiving portion includes and a pair of pin holes in the pair of tabs, and wherein the pair of pins disposed in the pair of pin holes is configured to extend into a corresponding pin slot.

10. A bone hook assembly adaptable to engage any one of a plurality of pedicle, lamina, or transverse process bones, each of the plurality of pedicle, lamina, or transverse process bones being dimensioned different than the other, the bone hook assembly comprising:
    a main body having a rod receiving portion;
    a jaw spaced apart from the main body so as to define a slot for receiving one of the plurality of pedicle, lamina, or transverse process bones, wherein the slot has a height;
    an actuator configured to adjust the height of the slot; and
    a receiving portion having elongated slots and a pair of tabs on the jaw;
    wherein the jaw is slidably attached to the main body;
    wherein the actuator is configured to fix the jaw with respect to the main body so as to adjust the height of the slot;

and wherein the receiving portion is configured to slidingly receive the jaw and the pair of tabs are configured to slide into a respective elongated slot.

11. The bone hook assembly as set forth in claim 10, further comprising a threaded bore on the receiving portion between the elongated slots.

12. The bone hook assembly as set forth in claim 11, wherein the actuator is a set screw threadingly engaged with the threaded bore such that a force is applied to bias the pair of tabs against the receiving portion, fixing the pair of tabs in place with respect to the receiving portion.

13. A bone hook assembly adaptable to engage any one of a plurality of pedicle, lamina, or transverse process bones, each of the plurality of pedicle, lamina, or transverse process bones being dimensioned different than the other, the bone hook assembly comprising:
a main body having a rod receiving portion;
a jaw spaced apart from the main body so as to define a slot for receiving one of the plurality of pedicle, lamina, or transverse process bones, wherein the slot has a height; and
an actuator configured to adjust the height of the slot;
wherein the jaw is slidably attached to the main body;
wherein the actuator is configured to fix the jaw with respect to the main body so as to adjust the height of the slot; and
wherein the actuator is a ratchet mechanism.

14. The bone hook assembly as set forth in claim 13, further comprising a receiving portion having an elongated slot and the jaw has a guide, and wherein the elongated slot extends the length of the receiving portion and the guide is configured to slidingly fit within the elongated slot.

15. The bone hook assembly as set forth in claim 14, further comprising a back wall of the receiving portion having a plurality of teeth.

16. The bone hook assembly as set forth in claim 15, wherein the plurality of teeth have a top contact surface and an angled surface extending from the top contact surface to the back wall.

17. The bone hook assembly as set forth in claim 16, further including a catch on the jaw including a lip at a distal end of the catch that is configured to engage the top contact surface of any one of the plurality of teeth.

* * * * *